United States Patent
Sanjoh (10) Patent No.: US 7,311,773 B2
(45) Date of Patent: Dec. 25, 2007

(54) BIOPOLYMER CRYSTAL MOUNTING DEVICE AND MANUFACTURING METHOD THEREOF

(75) Inventor: Akira Sanjoh, Kyoto-fu (JP)

(73) Assignee: Protein Wave Corporation, Kyoto-Fu (JP)

( * ) Notice: Subject to any disclaimer, the term of this patent is extended or adjusted under 35 U.S.C. 154(b) by 289 days.

(21) Appl. No.: 10/896,896

(22) Filed: Jul. 23, 2004

(65) Prior Publication Data

US 2005/0016442 A1    Jan. 27, 2005

(30) Foreign Application Priority Data

Jul. 25, 2003    (JP) ............................... 2003-201446

(51) Int. Cl.
*C30B 7/00*    (2006.01)
(52) U.S. Cl. .................... 117/68; 117/69; 117/70; 117/200; 117/201
(58) Field of Classification Search ............. 117/68, 117/69, 70, 200, 201; 422/245.1
See application file for complete search history.

(56) References Cited

U.S. PATENT DOCUMENTS 6,857,309 B2 * 2/2005 Mansky ..................... 73/64.49
2006/0086315 A1 * 4/2006 Thorne et al. ............. 117/209

FOREIGN PATENT DOCUMENTS

WO    WO/00/60345    * 10/2000

* cited by examiner

*Primary Examiner*—Robert Kunemund
(74) *Attorney, Agent, or Firm*—McDermott Will & Emery LLP (57) ABSTRACT

The invention provides a biopolymer crystal mounting device with which a biopolymer crystal having been grown in a solution containing a biopolymer can be taken out of the solution. The device can be manufactured efficiently without requiring labors and can be mass-produced with high yield. A biopolymer crystal mounting device comprises: a film member 12, which is made of a material possessing permeability to an electromagnetic wave, and which is integrally formed of a loop portion 16 holding a drop of solution containing a biopolymer crystal, a neck portion 18 and a body portion 20; and a tubular member 14 including a bearing hole 22 in which the body portion of the film member is inserted and supported. Further, the film member is inserted into and secured to the tubular member.

6 Claims, 9 Drawing Sheets

PRIOR ART

PRIOR ART

(a)

(b)

(c)

(d)

BIOPOLYMER CRYSTAL MOUNTING DEVICE AND MANUFACTURING METHOD THEREOF

BACKGROUND OF THE INVENTION

1. Field of the Invention

The present invention relates to a biopolymer crystal mounting device to be used for taking a biopolymer crystal out of a solution and mounting it at the time of providing the biopolymer crystal having been grown in the solution containing a biopolymer typically represented by a protein for use in crystallography, and to a method of manufacturing such device for mounting a crystal thereof.

2. Description of the Related Art

Making clear a three-dimensional structure of a biopolymer typically represented by a protein, not only enables to elucidate physiological functions of the biopolymer in vivo, but also is extremely useful for the purpose of advancing a rational development of drugs (drug design). As a practical method for analyzing a three-dimensional structure of the biopolymer, there have been an NMR (nuclear magnetic resonance) and an X-ray crystallography. From the viewpoint of analysis, the X-ray crystallography in which there is no restriction on a molecular weight of a biopolymer is considered especially effective from now on. In this X-ray crystallography, however, a single biopolymer crystal to be provided for use in the analysis has to be prepared. Moreover, to improve a resolution of the structure analysis, it is necessary to form a single crystal having a high crystallinity.

Figure 8:
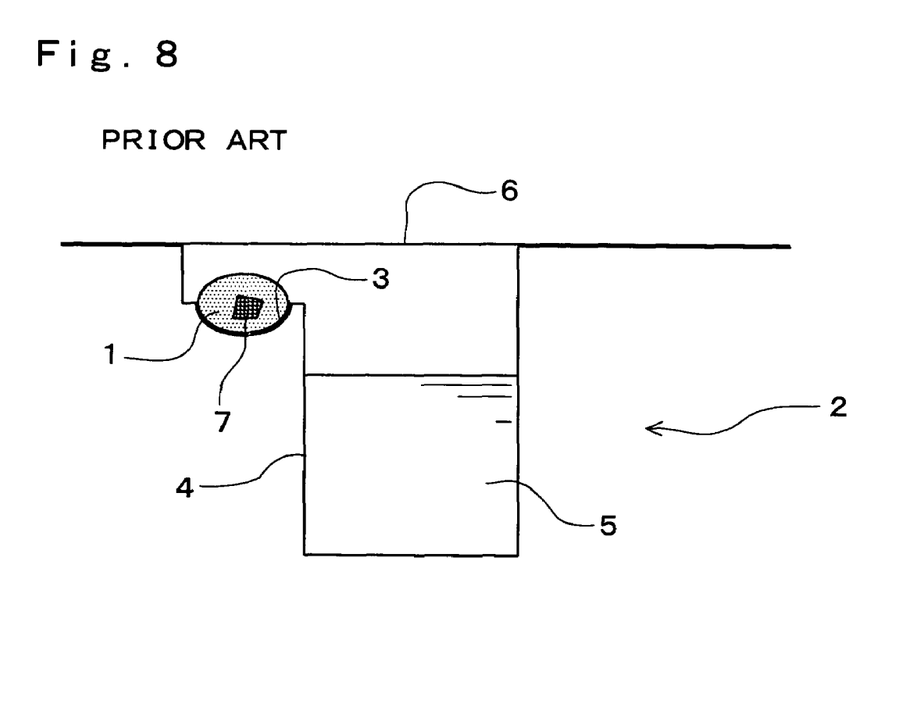
FIG. 8 is a schematic view for explaining the method of growing a single crystal of a protein according to the conventional sitting drop vapor diffusion method.

As a method for preparing a single biopolymer crystal such as protein, a vapor diffusion method is popularly employed these days. In a sitting drop vapor diffusion method, as shown in FIG. 8, a small volume of aqueous solution 1 of about 1 μl containing a protein is dropped into a concave part 3 of a well solution retention plate 2 (in a hanging drop vapor diffusion method, a small volume of aqueous solution 1 containing a protein is dropped onto a surface being a lower face side of a cover glass 6 and adhered thereto). Further, a precipitant 5 is contained in an inner bottom portion of a container-shaped concave part (well) 4, and a top opening of the container-shaped concave part 4 is closed tightly with the cover glass 6. Thus the aqueous solution 1 containing a protein comes to be in a supersaturated state due to evaporation of moisture in the course of time, and eventually a crystal 7 of the protein is precipitated in the foregoing aqueous solution 1.

After having obtained the crystal 7 of a protein, the crystal 7 is provided for use in crystallography. In the crystallography, a diffraction intensity of the crystal is measured using an X-ray diffraction measurement apparatus. Therefore it is required to get the crystal 7, which has grown within the aqueous solution 1, out of the concave part 3 of the well solution retention plate 2. Then, the crystal having been taken out is frozen with, e.g., liquid nitrogen, and thereafter this frozen crystal is irradiated with X-ray to collect X-ray diffraction data. A crystal of protein, however, is extremely soft inherently, and possesses brittle properties. In case where the taking out a crystal and treatments in each step of freezing thereof are defective when collecting X-ray diffraction data, the crystal having been grown all the way will be broken, or minute cracks will be made within the crystal, resulting in a trouble that data cannot be collected.

For that purpose, the following method has been widely employed. In this method, first as shown in FIG. 9(a), a tool 9 of such a structure as shown in FIG. 9(b) is fabricated by inserting a ring made of nylon, what is called as nylon loop (diameter thereof is approximately 1 mm or not more than 1 mm), into a support 8b made of metal, what is called as micro-tube, and securing it. Further, in the method, with the use of the mentioned tool 9, a biopolymer crystal is taken out of a solution, the crystal that is mounted on the ring 8a of the tool 9 is frozen, and thereafter X-ray diffraction data is collected. This method is described in more detail referring to FIG. 10. First, as shown in FIG. 10(a), the crystal 7 of a protein is picked up from the concave part 3 along with a part of the aqueous solution 1 with the use of the tool 9. Normally this operation is carried out manually under a microscope. Then, as shown in FIG. 10(b), the crystal 7 of a protein is retained along with the aqueous solution 1 in the ring 8a of the tool 9. Next, though not shown, the ring 8a of the tool 9 on which the crystal 7 is retained is dipped into a defrost (i.e., anti-freezing agent), whereby, as shown in FIG. 10(c), moisture of the aqueous solution 1, which is retained within the ring 8a of the tool 9, is substituted with a defrost 1'. Thereafter, as shown in FIG. 10(d), to protect the crystal 7, a liquid nitrogen gas stream F is sprayed obliquely from above to the crystal 7 retained within the ring 8a of the tool 9, and the crystal within the ring 8a is made to freeze. Subsequently, the crystal 7 of a protein retained in the ring 8a of the tool 9 is irradiated with X-ray from the side, and the measurement of diffraction intensity is carried out (see, for example, S. Ohno, S. Yano (eds.), (ed, Chemical Society of Japan) "Basic Course 12 for Chemists, X-ray Structure Analysis" Asakura Co., pp. 102-108, March, 1999).

As described above, according to the conventional method of using the tool 9 that is fabricated by securing a ring (nylon loop) 8a to a support (micro-tube) 8b, there exist several problems in practical use as described hereinafter.

(1) The tool 9 shown in FIG. 9(b) is normally manufactured manually. That is, as shown in FIG. 9(a), the tool 9 is manufactured by first tying up nylon fibers into a bundle to form into a ring shape and twisting both end portions of the nylon fiber bundle with each other to fabricate a nylon loop, and thereafter inserting the twisted portion of the nylon loop into the micro-tube and securing it thereto with an adhesive or the like. Since the tool 9 is manually fabricated in such a way, the fabrication thereof is extremely inefficient, and requires much time. Moreover, a burden of labors on a worker is large in the manual fabrication. Furthermore, a loop may be manufactured to be inaccurate in diameter resulting in the reduction in yield. A further problem exists in that the tool 9 cannot be mass-produced since the tool 9 is fabricated in manual works.

(2) Since fibers forming a nylon loop is approximately 10 μm to 20 μm in diameter, as shown in FIG. 10(d), the nylon loop is vibrated due to the wind pressure of a liquid nitrogen gas stream F when a crystal is retained in the ring 8a of the tool 9 and the crystal is frozen, leading to a further problem that diffraction data cannot be collected.

SUMMARY OF THE INVENTION

The present invention was made in consideration of the circumstances as discussed above, and has an object of providing an apparatus for a mounting biopolymer crystal, being an apparatus taking the place of the tool having been conventionally used for the purpose of taking a biopolymer crystal having been grown in a solution containing a biopolymer out of the solution, which can be manufactured efficiently without requiring labors, achieving a high yield, and which is capable of being mass-produced and improving effectiveness and accuracy in crystallography. Further, the invention has another object of providing a manufacturing method of a biopolymer crystal mounting device by which such a biopolymer crystal mounting device mounting can be successfully manufactured.

The invention according to claim 1 provides a biopolymer crystal mounting device for taking out and mounting a biopolymer crystal having been grown in a solution containing the biopolymer along with a part of the solution, and providing it for use in crystallography, comprises a film member that is made of a material having permeability to an electromagnetic wave and that is integrally formed of an annular mounting portion for mounting a drop of solution containing the biopolymer crystal and a support portion joined thereto.

In the biopolymer crystal mounting device of the invention according to claim 1, a biopolymer crystal having been grown in a solution containing the biopolymer is mounted and taken out along with a part of the solution with an annular mounting portion of a film member. The biopolymer crystal having been taken out of the solution is provided for use in crystallography as in the state of being mounted in the annular mounting portion since the film member is made of a material possessing permeability to an electromagnetic wave. The film member forming the biopolymer crystal mounting device can be manufactured of a synthetic resin film by photo-etching, e.g., using a photomechanical apparatus efficiently as well as without requiring labors.

As a result, with the use of the biopolymer crystal mounting device of the invention according to claim 1, it is possible to reliably take the biopolymer crystal having been grown in the solution containing the biopolymer out of the solution. Further, it is possible for the film member mounting the crystal to have a certain degree of rigidity, thereby enabling to improve effectiveness and accuracy in crystallography. Furthermore, this biopolymer crystal mounting device can be manufactured efficiently as well as without requiring labors, and can be mass-produced with a high yield.

The invention according to claim 2 provides the biopolymer crystal mounting device as defined in claim 1, in which the mentioned support portion of the film member is shaped into an elongated triangle.

In the biopolymer crystal mounting device of the invention according to claim 2, a support portion of a film member is elongate triangle-shaped, so that it is possible to improve rigidity of the film member to an external force such as wind pressure of a liquid nitrogen gas stream that is applied when freezing the crystal by curving the support portion along a longitudinal direction thereof. As a result, it is possible to suppress flexure and vibration of the support portion and annular mounting portion joined thereto due to the action of external force.

The invention according to claim 3 provides the biopolymer crystal mounting device as defined in claim 1, which is provided with a tubular member including a bearing hole in which the mentioned support portion of the film member is inserted and supported, and in which the mentioned film member is connected and secured to the mentioned tubular member.

In the biopolymer crystal mounting device of the invention according to claim 3, the support portion of the film member is inserted into a bearing hole of the tubular member, and the film member is connected and secured to the tubular member, so that it becomes easy to mount the apparatus on the mounting portion of an X-ray diffraction measurement apparatus. Furthermore, when the support portion of the film member is inserted into the bearing hole of the tubular member in the state of being curved along a longitudinal direction thereof and the film member is connected and secured to the tubular member, it is possible to improve rigidity of the film member to external force. As a result, it is possible to suppress more reliably the flexure and vibration of the annular mounting portion joined to the support portion due to the action of external force.

The invention according to claim 4 provides the biopolymer crystal mounting device as defined in any one of claims 1 through 3, and in which the mentioned film member is formed using a polyimide film by photo-etching.

In the biopolymer crystal mounting device of the invention according to claim 4, it is possible to easily fabricate a film member of the biopolymer crystal mounting device using a polyimide film by photo-etching.

The invention according to claim 5 provides a method of manufacturing a biopolymer crystal mounting device for taking out and mounting a biopolymer crystal having been grown in a solution containing the biopolymer along with a part of the solution and providing it for use in crystallography, and in which by employing a film raw material and applying photo-etching to the mentioned film raw material, a film member in which a support portion is joined to an annular mounting portion mounting a drop of solution containing a biopolymer crystal is obtained.

In the manufacturing method of a biopolymer crystal mounting device of the invention according to claim 5, by applying a photo-etching process to the film member, it is possible to manufacture comparatively with ease a film member of the biopolymer crystal mounting device of the invention according to claim 1.

The invention according to claim 6 provides the manufacturing method as defined in claim 5, and in which a sheet of film raw material is formed into a plurality of film members being arranged in a row so that respective film members can be cut off.

In the manufacturing method of the invention according to claim 6, a plurality of film members can be obtained at the same time from just one sheet of film raw material, and these film members having been obtained can be used by cutting off each of them. As a result, it is possible to mass-produce the film member of the biopolymer crystal mounting device.

The invention according to claim 7 provides the manufacturing method as defined in claim 5, and in which a sheet of film raw material is formed in to plural types of film members of which annular mounting portions are different in size In the manufacturing method of the invention according to claim 7, it is possible to manufacture at the same time plural types of film members of which annular mounting portions have different sizes from just one sheet of film raw material.

The invention according to claim 8 provides the manufacturing method as defined in any one of claims 5 through 7, and in which a polyimide film is employed as a film raw material.

In the manufacturing method of the invention according to claim 8, it is possible to obtain a film member of the biopolymer crystal mounting device from a polyimide film.

BRIEF DESCRIPTION OF THE INVENTION

FIG. 2(*a*) is an exploded perspective view of a biopolymer crystal mounting device provided with the film member shown in FIG. 1, and FIG. 2(*b*) is a perspective view of an assembly of the foregoing biopolymer crystal mounting device.

FIGS. 3(*a*), (*b*), (*c*), (*e*) are schematic views each for explaining operations of taking out a crystal and collecting X-ray diffraction data with the use of the biopolymer crystal mounting device shown in FIGS. 1 and 2.

FIGS. 5(*a*), (*b*), (*c*), (*d*), (*e*) are schematic enlarged cross sectional views each for explaining an example of the manufacturing method of a film member of the biopolymer crystal mounting device shown in FIGS. 1 and 2.

FIGS. 6(*f*), (*g*), (*h*) are schematic enlarged cross sectional views each for explaining an example of the manufacturing method of the same film member.

FIGS. 9(*a*) and (*b*) is a schematic view of the conventional tool employed for taking a biopolymer crystal out of a solution and providing it for use in X-ray structure analysis.

FIGS. 10(*a*), (*b*), (*c*) and (*d*) are a schematic view for explaining operations of taking out the crystal and collecting X-ray diffraction data with the use of the tool shown in FIG. 9.

DESCRIPTION OF THE PREFERRED EMBODIMENTS

Several preferred embodiments according to the present invention are hereinafter described referring to FIGS. 1 through 7.

Figure 1:
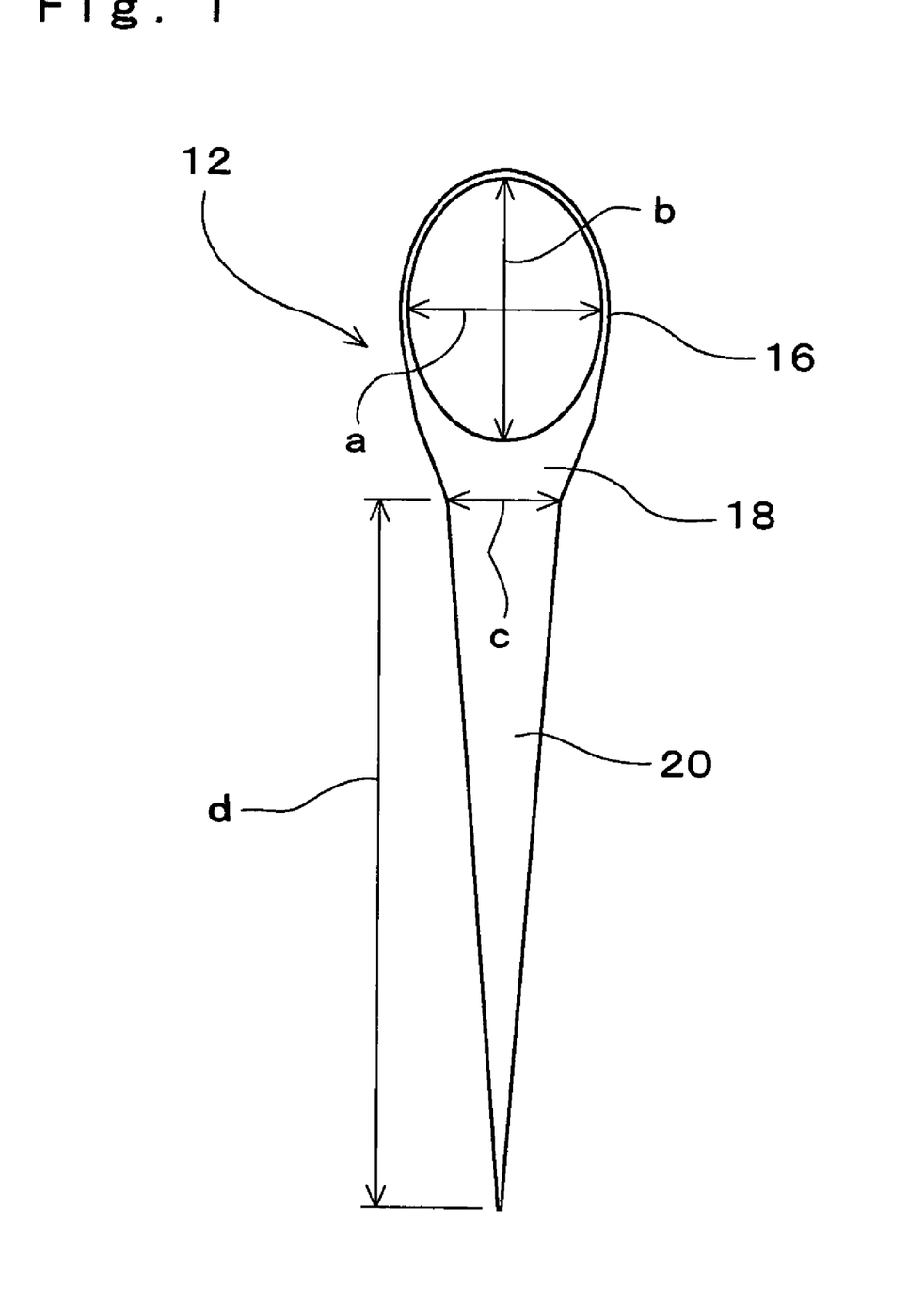
FIG. 1 shows a preferred embodiment according to the present invention, and is a plan view of a film member being one component of a biopolymer crystal mounting device to be used for mounting a crystal at the time of providing the biopolymer crystal for use in X-ray crystallography.
Figure 2:
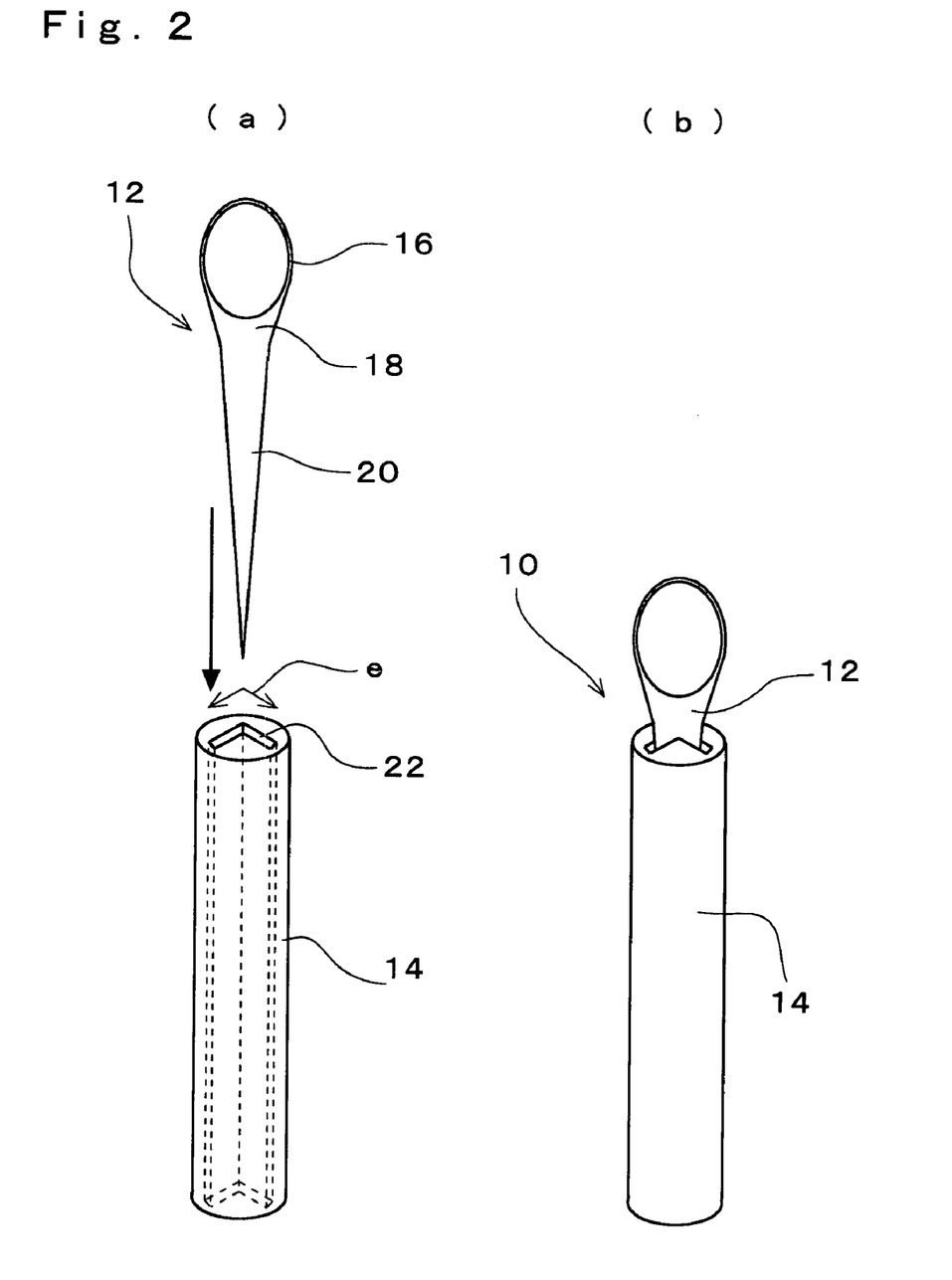

FIGS. 1 and 2 show an embodiment of the invention. FIG. 1 is a plan view of a film member, being a component of a biopolymer crystal mounting device (hereinafter, referred to as "device") to be used for mounting a crystal at the time of providing the biopolymer crystal, for example, protein for use in X-ray crystallography. FIG. 2(*a*) is an exploded perspective view of the device, and FIG. 2 (*b*) is a perspective view of an assembled device. This device indicated by 10 consists of a film member 12 possessing a function of mounting a crystal, and a tubular member (micro-tube) 14 acting as a portion holding this film member 12 and setting it onto a mounting part of an X-ray diffraction measurement apparatus.

The film member 12 is made of material, e.g., synthetic resin including high permeable properties to an electromagnetic wave, especially to X-ray. Thus, the film member 12 enables the crystal of a protein having been grown in a solution containing the protein to be taken out and mounted along with a part of the solution, and provided as it is for use in X-ray diffraction measurement. Furthermore, the film member 12 is made of material of high chemical resistance and high waterproof. This film member 12 is fabricated by machining a membrane film raw material, specifically, as described later, by photo etching a film raw material such as polyimide film. The film member 12 is a membrane film integrally formed of a loop portion (annular mounting portion) 16 including an aperture area mounting a drop of solution containing a protein crystal having been grown; a neck portion 18 that is joined to the loop portion 16 to improve a mechanical strength of the loop portion 16; and a body portion (support) 20 that is joined to the neck portion 18. The body portion 20 possesses an elongated isosceles triangle shape in the shown example, and is a portion functioning to secure the film member 12 to the tubular member 14, being a separate member as described later.

An aperture area of the loop portion 16 can be of various sizes in accordance with a size of a protein crystal having been grown. Plural types of film members 12 having different sizes of aperture area of the loop portion 16 are prepared. That is, with reference to FIG. 1, when letting a dimension of a minor axis of aperture area of the loop portion 16 "a" and a dimension of a major axis "b", an average diameter of an aperture area D will be (a+b)/2. Further, various film members 12 having the foregoing different average diameters are fabricated, whereby it comes to be possible to take out and mount a variety of sizes of protein crystals. In this case, it is necessary that an average diameter D of the loop member 16 of the film member 12 for use in stably mounting a protein crystal is made larger than a size of a protein crystal.

The tubular member 14 is loaded with the film member 12, and is made of, e.g., stainless steel. In this tubular member 14, as shown in FIG. 2(*a*), a bearing hole 22 into which the body portion 20 of the film member 12 is inserted and supported is formed so as to extend in axial direction. Although it is preferable that a cross sectional shape of the bearing hole 22 is, e.g., circle, the bearing hole 22 in the shown example has a dogleg shape. The reason why a cross sectional shape of the bearing hole 22 is a dogleg shape is as follows:

① Supposing that across sectional shape of the bearing hole 22 is a circle, the body portion 20 of the film member 12 having been once inserted is likely to get out of the bearing hole 22. Accordingly, there is a possibility that the film member 12 will be dropped out of the tubular member 14 in the process of mounting operation of a protein crystal. Whereas, when the bearing hole 22 is dogleg-shaped in cross section, the body portion 20 of the film member 12 is curved along a longitudinal direction thereof to be pressed to an inner wall surface of the bearing hole 22, thereby preventing the film member 12 from being dropped out of the tubular member 14.

② Supposing that a cross-sectional shape of the bearing hole 22 is a circle, when inserting the film member 12 into the tubular member 14, the body portion 20 of the film member 12 having been inserted comes to be in an unstable state, and the film member 12 may incline overall with respect to the axis of the tubular member 14. Thus, it becomes necessary to adjust an angle of the film member 12 again after having inserted the film member 12 in the tubular member 14. Whereas, by making a cross section of the bearing hole 22 dogleg-shaped, the body portion 20 goes to an innermost portion of the bearing hole 22 as the body portion 20 slides in contact with an inner wall surface of the bearing hole 22 at the time of inserting the body portion 20 of the film member 12 into the bearing hole 22 of the tubular member 14. Therefore, a longitudinal direction of the film member 12 is coincident with an axial direction of the tubular member 14 at all times. Accordingly, it is unnecessary to adjust an angle of the film member again after the film member 12 has been inserted in the tubular member 14.

As shown in FIG. 2(*b*), when the film member 12 is inserted in and connected to the tubular member 14, the film member 12 and the tubular member 14 are secured to each other with, e.g., an adhesive, not shown, at a position of the body portion 20 or the neck portion 18 of the film member 12.

Figure 3:
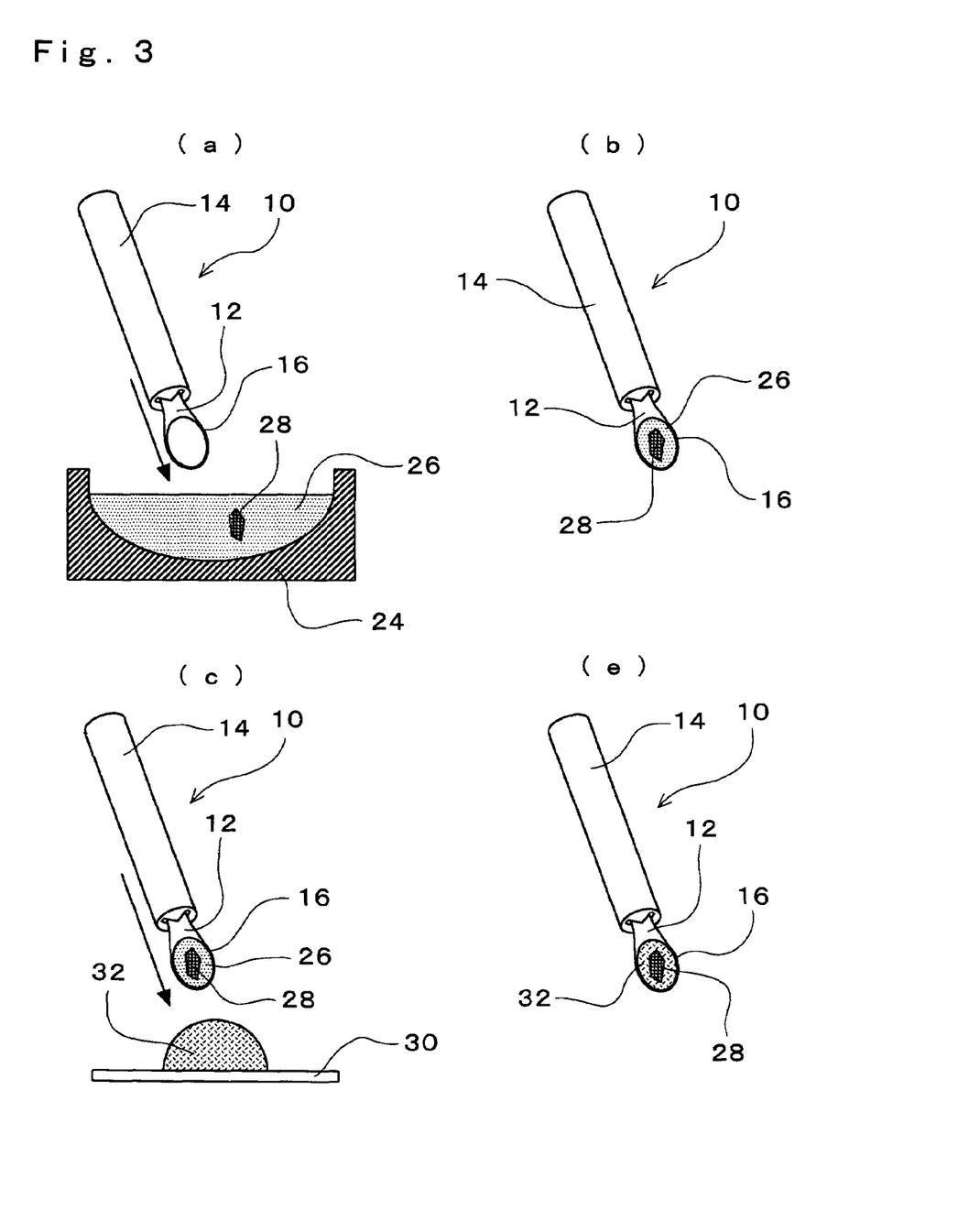
Figure 4:
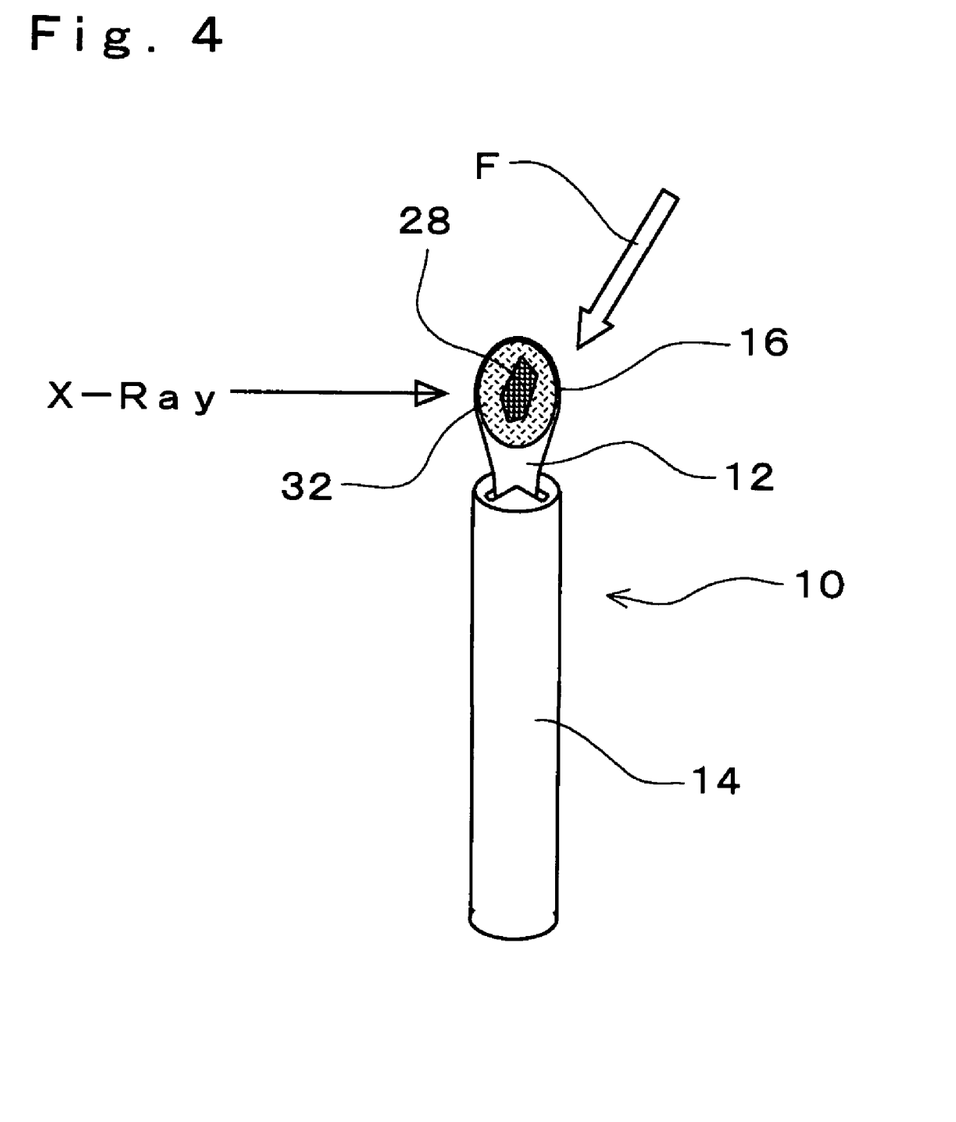
FIG. 4 is a schematic view for explaining operations of taking out a crystal and collecting X-ray diffraction data with the use of the same biopolymer crystal mounting device.

The device 10 that is fabricated as described above is used in the same manner as in the above-described conventional tool 9. That is, first, as shown in FIG. 3 (*a*), using the device 10, a protein crystal 28 having been grown in a protein solution 26 that is contained in a crystallization well 24 is picked up from the crystallization well 24 along with a part of the protein solution 26. The protein crystal 28 having been picked up from the protein solution 26, as shown in FIG. 3(*b*), is mounted on the loop portion 16 of the film member 12 along with a drop of protein solution 26. Next, as shown in FIG. 3(*c*), the loop portion 16 of the film member 12 of the device 10 on which the protein crystal 28 is mounted, is dipped in a defrost 32 retained on a support plate 30. Thus, as shown in FIG. 3(*d*), the protein solution 26 retained within the loop portion 16*b* of the film member 12 of the device 10 is substituted with the defrost 32. Thereafter, as shown in FIG. 4, to protect the protein crystal 28, a liquid nitrogen gas stream F is sprayed obliquely from above to the protein crystal 28 in the loop portion 16 of the film member 12 of the device 10 to freeze the protein crystal 28 within the loop portion 16. Then, the protein crystal 28 that is held in the loop portion 16 of the film member 12 of the device 10 is irradiated from the side with X-ray to carry out the measurement of diffraction intensity.

Now, an example of the manufacturing method of a film member 12 of the foregoing device 10 is described with reference to FIGS. 5 and 6.

Figure 5:
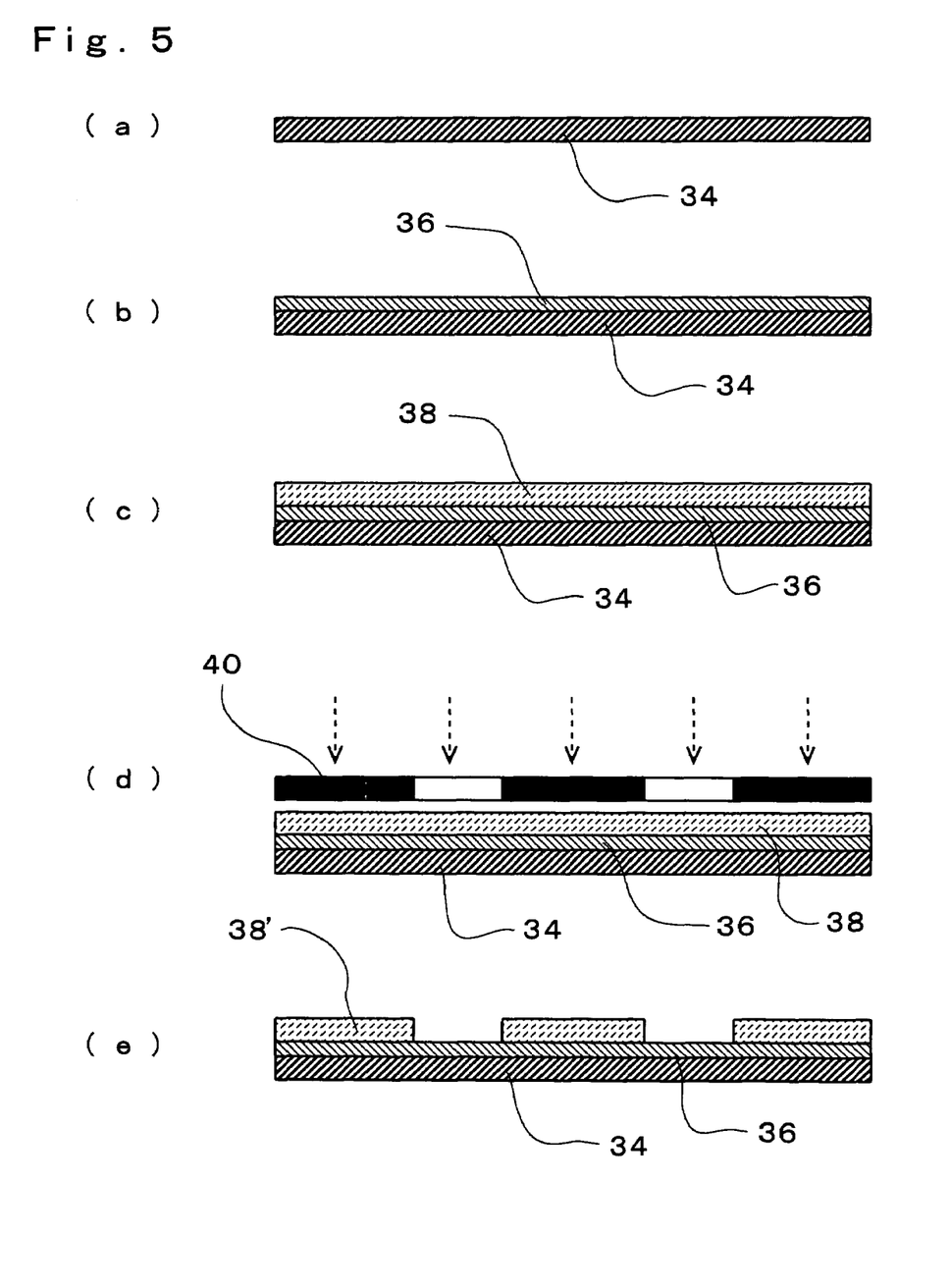

(1) First, a membrane film 34 is prepared (FIG. 5(*a*)). This film 34 is preferably in a range of 1 μm to 1 mm in membrane thickness, more preferably, 5 μm to 100 μm and, most preferably, 10 μm to 50 μm. Any material can be employed as the film 34 as long as the material possesses high chemical resistance and high heat resistance. However, for example, a polyimide film is preferably used.

(2) A metal thin-film acting as a metal mask is formed on the surface of the film 34 by vapor deposition or sputtering (FIG. 5(*b*)). The metal mask is used as a mask material at the time of etching the film 34 into a desired pattern. Any material can be employed as the metal thin-film 36 as long as the material can be formed into a thin-film by the vapor deposition or sputtering. However, for example, Ni, Cr, Al, Ti, W, Cu, or an alloy containing these metals is preferably used. Furthermore, it is preferable that the metal thin-film 36 is within a range of, for example, about 10 nm to about 1 μm in thickness.

(3) Subsequently, a photo-resist film 38 is formed on the surface of the metal thin-film 36 (FIG. 5(*c*)). It is preferable that the photo-resist film 38 is within a range of, for example, 0.1 μm to 10 μm in thickness. In addition, in this embodiment, a positive type resist is used as a photo-resist.

(4) The photo-resist film 38 is exposed to ultraviolet rays via the mask 40 having a predetermined pattern with the use of a photolithography.

(5) The photo-resists film 38 is developed after having been exposed to form a corrosive resistant resist film 38' having a predetermined pattern (FIG. 5(*e*)).

Figure 6:
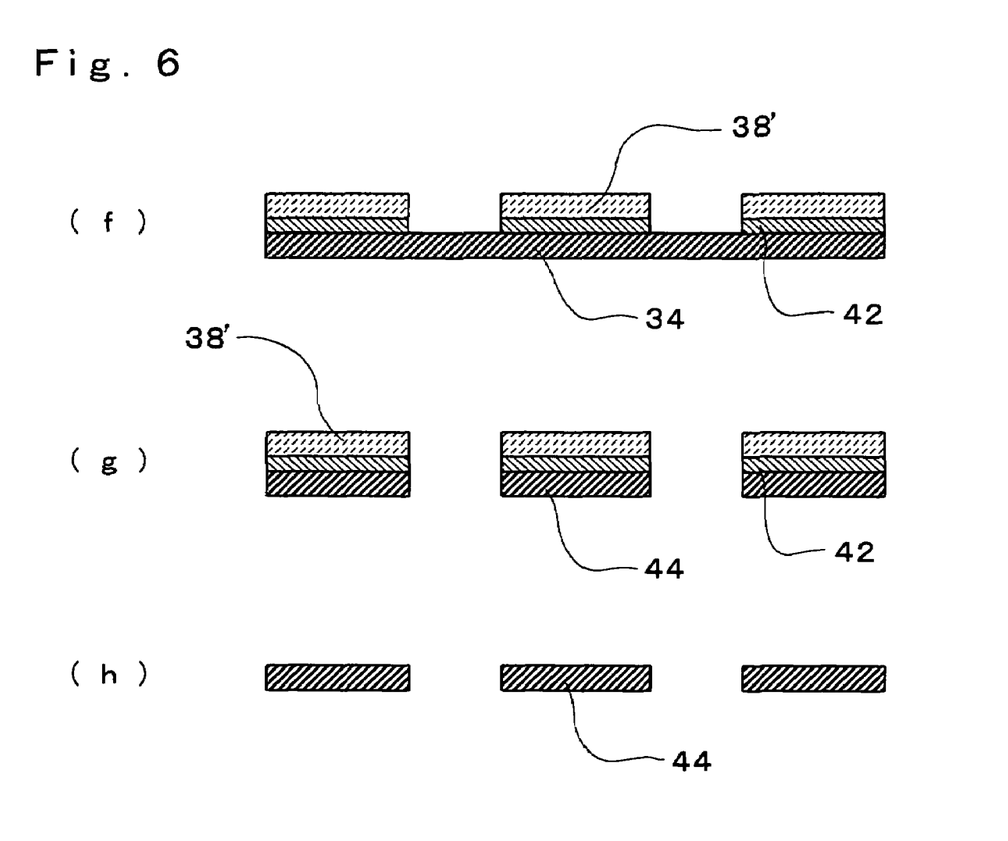

(6) The metal thin-film 36 is etched using the corrosive resistant resist film 38' having been developed in a predetermined pattern as a mask to form a metal mask 42 possessing a predetermined pattern (FIG. 6(*f*)).

(7) The film 34 is etched in a predetermined pattern using the metal mask 42 as a mask by dry etching or wet etching (FIG. 6(*g*)). In the dry etching method, for example, fluorocarbon gas is used, and the processing is carried out using a reactive ion etching apparatus. In the wet etching method, the processing is carried out with the use of, for example, an alkaline aqueous solution.

(8) The corrosive resistant resist film 38' is peeled using a thin-film liquid, and then the metal mask 42 is dissolved and removed with an etching liquid. Thus, a film member 44 of a desired configuration can be obtained (FIG. 6(*h*)).

Figure 7:
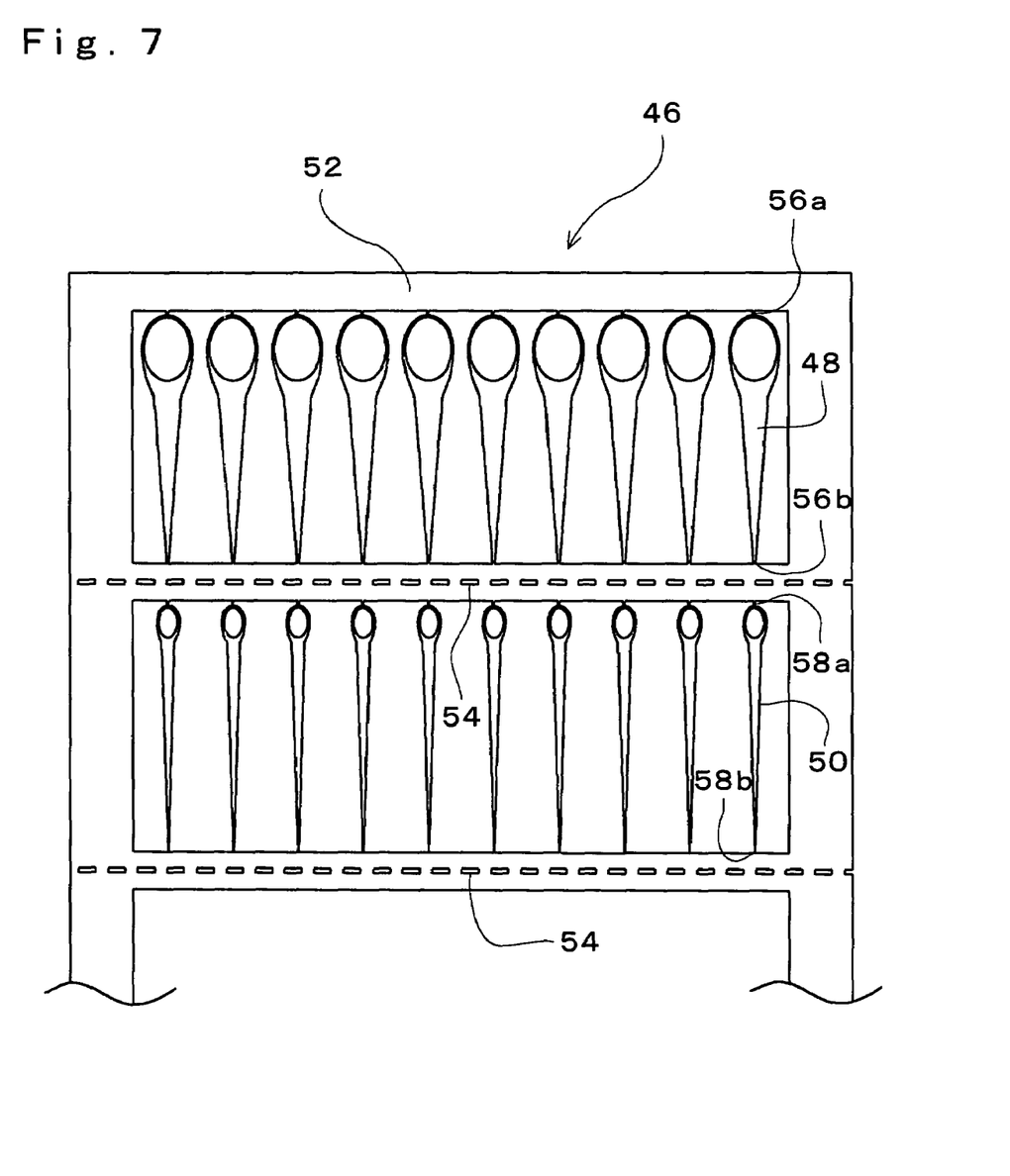
FIG. 7 shows another embodiment of the invention, and is a plan view of a film material including a plurality of film members prepared from a sheet of film raw material.

FIG. 7 is a plan view of a film material including a plurality of film members having been fabricated from one sheet of film raw material. In this film material 46, a plurality of film members 48, 50 are formed. The plural types of (two types in this embodiment) film members 48, 50 having different average diameters of an aperture area of a loop portion are formed respectively in the film material 46. The plurality of film members 48, 50 each group of which has the same average diameter of the loop portion are located each in a row. A cut line 54 is formed in a frame portion 52 of the film material between the row of film members 48 and the row of film members 50 of which loop portions are different in size. Thus, each row of film members 48, 50 of which loop portions are different in size can be separated from each other. Furthermore, each row of respective film members 48, 50 are connected to the frame portion 52 of the film member 46 with a thin line part (it is referred to as "tie-bar") 56*a*, 56*b*; 58*a*, 58*b* respectively at upper ends and lower ends. Then, the film members 48, 50 can be mechanically separated from the frame portion 52 with ease individually. According to the embodiment shown in this FIG. 7, the film members 48, 50 can be mass-produced; and further the film members 48, 50 of which loop portions are different in size can be massively fabricated at the same time.

EXAMPLES

Hereinafter, more specific examples according to the invention are described.

[Example of Fabrication of Device]

As a starting material, a square-shaped polyimide film having a 25 μm thickness and a side dimension of 120 mm was employed. This polyimide film was machined into a film member 12 of a pattern configuration as shown in FIG. 1. The loop portion 16 of the film member 12 was formed to be in the following sizes: a=0.8 mm; b=1.2 mm; average diameter D=1.0 mm. The minimum line width forming the loop portion 16 was 10 μm. Besides, a width c of the neck portion 18 was 0.6 mm, and a length d of the body portion 20 was 3 mm. Such a film member 12 was manufactured in the method as follows.

The above-mentioned polyimide film was mounted on and secured to a glass substrate of 1 mm in thickness. A metal thin-film of Ni·Cr alloy of 100 nm in film thickness was formed on the surface of this polyimide film by sputtering. Next, a positive type photo-resist was applied onto the metal thin-film by spin coating, and therafter was subjected to baking treatment to form a photo-resist film of 1 μm in thickness on the surface of the metal thin-film. Subsequently, the photo-resist film was subjected to pattern exposure by photolithography, and thereafter developed to form a positive type corrosive resistant film. Then, the metal thin-film was etched with the use of hydrochloric acid etching liquid. A metal mask having a predetermined pattern was obtained by carrying out the above-described process, and subsequently etching of the polyimide film was performed using a dry etching apparatus. This etching was carried out under the conditions that reaction pressure was 0.1 mTorr, and RF power was 1 KW with the use of a mixed gas ($CF_4:O_2=2:1$) of $CF_4$ gas (chlorofluorocarbon) and $O_2$ gas (oxygen). After completing the etching of polyimide film, a resist film and a metal mask left on the surface were removed by etching. In the film member having been fabricated in the above-described manner, a line width of an annular portion forming the loop portion was 12 μm.

Subsequently, as shown in FIG. 2(a), using a drill of 100 μm in diameter, a through hole was provided through into a stainless steel tube of 0.65 in diameter and 50 mm in length, thereby forming a tubular member (micro-tube) 14. An angle (angle between two sides forming a dogleg shape) of an opening of the bearing hole of the tubular member 14 was 120°, and e=0.7 mm.

Then, as shown in FIG. 2(b), the body portion 20 of the film member 12 was inserted in the bearing-hole 22 of the tubular member 14 up to a boundary position between the body portion 20 and the neck portion 18, and thereafter the film member 12 was bonded and secured to the tubular member 14 using an epoxy resin eventually completing the fabrication of the device 10.

[Crystallization Test]

An elastase made from the bovine pancreas was dissolved into an ammonium acetate buffer solution of 0.1M and pH4.6 in concentration so as to be a concentration of 10 mg/ml, thus an aqueous solution containing a protein being prepared. At the same time, NaCl was dissolved into an ammonium acetate buffer solution of 0.1M and pH4.6 in concentration so that a resultant mixture thereof was 1.5M in concentration, thus a precipitant being prepared.

The above-mentioned precipitant of 500 μl was dropped into a reservoir within a sitting drop plate. Then, each 1.0 μl of the above-mentioned protein solution and precipitant was dispensed respectively into a crystallization well in the sitting drop plate. A crystallization test was carried out under the conditions that the whole protein solutions were retained in the crystallization well for four days at a temperature of 20° C. Thereafter, when observing the solution in the crystallization well, three crystals each size of which was approximately 0.3 mm has been grown.

COMPARATIVE EXAMPLE

Figure 9:
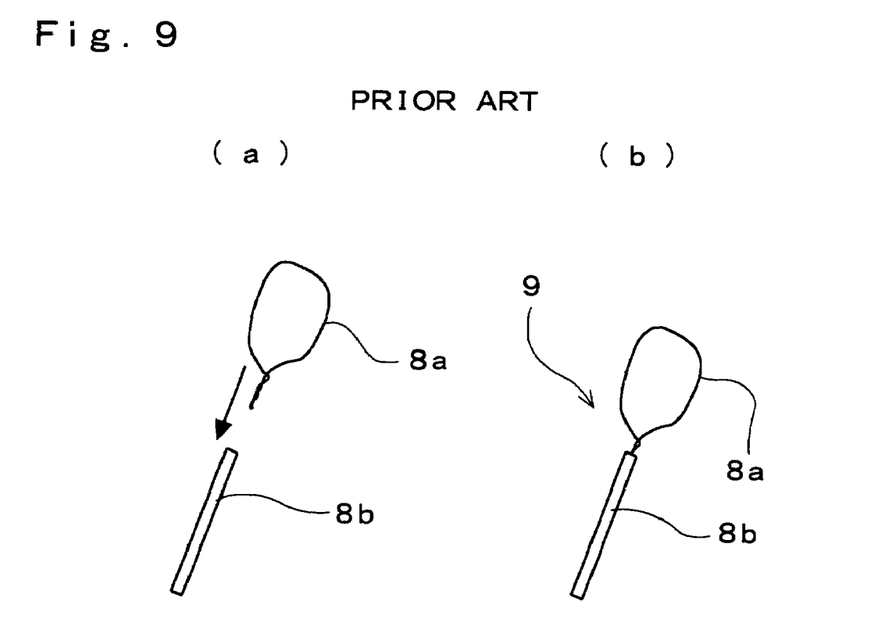
Figure 10:
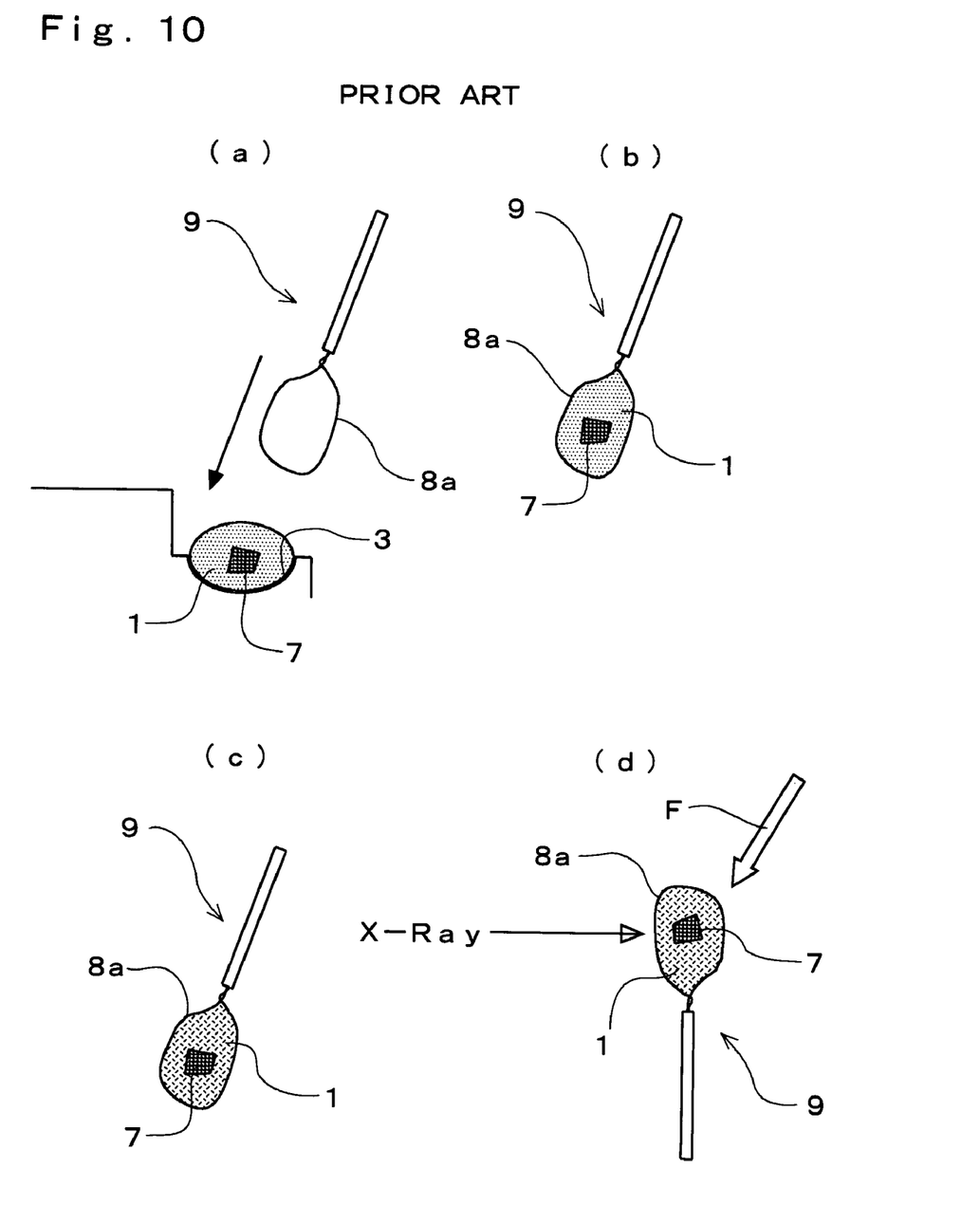

Taking Out Crystal and Collection of Diffraction Data Using the Conventional Tool One crystal of the elastase made from the bovine pancreas having been obtained as described above [in crystallization test] was taken out of the protein solution with the use of the conventional tool 9 shown in FIGS. 9 and 10. A nylon loop of 1 mm in diameter was employed. The crystal having been grown was mounted on the nylon loop of the tool and removed, and was immediately dipped in a defrost for 3 seconds. The defrost was prepared by dissolving $Li_2SO_4$ into an ammonium acetate buffer solution of 0.1M and pH4.6 in concentration so as to be 3M in concentration after mixing. The solution was substituted with the defrost of such a composition. Thereafter the tool was set into the mounting portion of an X-ray diffraction measurement apparatus, and the crystal was frozen with a liquid nitrogen gas stream eventually to collect X-ray diffraction data. As a result of analyzing the X-ray diffraction data having been collected, there was little background resulted from the frozen water, and a good resolution of 2.8 Å was obtained.

[Removal of Crystal and Collection of Diffraction Data Using the Device]

One crystal of elastase made from the bovine pancreas having been obtained as described above in the crystallization test was taken out of the protein solution with the use of the device. Thereafter, the crystal was immediately dipped in a defrost for 3 seconds. The composition of the defrost was the same as that was used in the above-mentioned comparative example. The solution was substituted with this defrost. Thereafter the present device was set into the mounting portion of an X-ray diffraction measurement apparatus, and the crystal was frozen with a liquid nitrogen gas stream eventually to collect X-ray diffraction data. As a result of analyzing the X-ray diffraction data having been collected, in the same manner as in the above-mentioned results of comparative example, there was little background resulted from the frozen water, and a good resolution of 2.8 Å was achieved.

What is claimed is:

1. A method of manufacturing a biopolymer crystal mounting device for taking out and mounting a biopolymer crystal having been grown in a solution containing the biopolymer along with a part of the solution and providing it for use in crystallography, comprising the steps of:

forming a sheet comprising a plurality of film members, by employing a film raw material and applying photo-etching to said film raw material, said film members comprise a support portion joined to an annular mounting portion for mounting a drop of solution containing a biopolymer crystal, wherein the film members are formed into a plurality of types having different sized annular mounting portions on said sheet, and the film members are arranged into rows so that respective film members can be cut off from said sheet.

2. The method of manufacturing a biopolymer crystal mounting device according to claim 1, wherein a polyimide film is employed as a film raw material.

3. A method of manufacturing a biopolymer crystal mounting device for taking out and mounting a biopolymer crystal having been grown in a solution containing the biopolymer along with a part of the solution and providing it for use in crystallography, providing a film member comprising a support portion joined to an annular mounting portion for mounting a drop of solution containing a biopolymer crystal; and inserting said support portion into a bearing hole in a support member, wherein a cross sectional shape of said bearing hole is dogleg-shaped.

4. The method according to claim 3, wherein said support member is a tubular member.

5. The method according to claim 3, further comprising applying an adhesive between said film member and said support member to secure said film member to said support member.

6. A method of manufacturing a biopolymer crystal mounting device for taking out and mounting a biopolymer crystal having been grown in a solution containing the biopolymer along with a part of the solution and providing it for use in crystallography, the biopolymer crystal mounting device comprising a film member having permeability to x-ray radiation, and integrally formed of an annular mounting portion for mounting a drop of solution containing the biopolymer crystal and a support portion joined thereto, comprising the steps of:
- providing a membrane film having permeability to x-ray radiation;
- forming a metal film on said membrane film by vapor deposition or sputtering;
- forming a photoresist film on said metal film;
- patterning said photoresist film to expose portions of the metal film;
- etching the exposed portions of the metal film to expose portions of the membrane film underlying said exposed portions of the metal film;
- removing the remaining photoresist film; and
- removing the remaining metal film.

* * * * *